US006280941B1

(12) United States Patent
Tsao et al.

(10) Patent No.: US 6,280,941 B1
(45) Date of Patent: Aug. 28, 2001

(54) GENETIC MARKER TEST FOR LUPUS

(75) Inventors: Betty P. Tsao, Los Angeles; Rita M. Cantor, Rolling Hills Estates; Jerome I. Rotter, Los Angeles, all of CA (US)

(73) Assignees: Cedars-Sinai Medical Center, Los Angeles; The Regents of the University of California, Oakland, both of CA (US)

( * ) Notice: Subject to any disclaimer, the term of this patent is extended or adjusted under 35 U.S.C. 154(b) by 0 days.

(21) Appl. No.: 09/280,181

(22) Filed: Mar. 29, 1999

(51) Int. Cl.$^7$ ............................. C12Q 1/68; C12P 19/34; C07H 21/04

(52) U.S. Cl. ............................. 435/6; 435/91.2; 435/810; 536/23.2; 536/24.31; 536/24.33

(58) Field of Search ................................. 435/6, 15, 91.2, 435/194, 810; 536/23.2, 24.31, 24.33

(56) References Cited

PUBLICATIONS

Alkhatib, H.M. et al., "Cloning and expression of cDNA for human poly(ADP–ribose) polymerase", *Proc. Natl. Acad. Sci. USA*, 84: 1224–1228, Mar. 1987.

Cherney, B.W., et al., "cDNA sequence, protein structure, and chromosomal location of the human gene for poly(ADP–ribose) polymerase", *Proc. Natl. Acad. Sci. USA*, 84: 8370–8374, Dec. 1987.

Dib, C. et al., "A comprehensive genetic map of the human genome based on 5,264 microsatelllites", *Nature*, 380: 152–154, Mar. 14, 1996.

Suzuki, H. et al., "Molecular cloning of cDNA for human poly(ADP–ribose) polymerase and expression of its gene during HL–60 cell differentiation", *Biochemical and Biophysical Research Communications*, 146(2): 403–409, Jul. 31, 1987.

Kotzin, B.L., "Systemtic Lupus Erythematosus", *Cell*, 85: 303–306, May 3, 1996.

Ogura, T. et al., "Characterization of a putative promoter region of the human poly(ADP–ribose) polymerase gene: structural similarity to that of the DNA polymerase β gene", *Biochemical and Biophysical Research Communications*, 167(2): 701–710, Mar. 16, 1990.

Trucco, C. et al., "Mutations in the amino–terminal domain of the human poly(ADP–ribose) polymerase that affect its catalytic activity but not its DNA binding capacity", *FEBS Letters*, 399: 313–316 (1996).

Yokoyama, Y. et al., "Human poly(ADP–ribose) polymerase gene", *Eur. J. Biochem.*, 194: 521–526 (1990).

Abe, M., et al., "In vitro spontaneous and UVB–induced lymphocyte apoptosis are not specific to SLE", *Photodermatol. Photoimmunol. Photomed.*, 13(5–6): 204–207, Oct.–Dec. 1997.

Auer, B. et al., "Human nuclear NAD+ ADP–ribosyltransferase(polymerizing): organization of the gene", *DNA* 8(8): 575–80, Oct. 1989, Abstract only.

Calvo–Alen, J. et al., "Identification of patient subsets among those presumptively diagnosed with, referred, and/or followed up for systemic lupus erythematosus at a large tertiary care center", *Arthritis Rheum.*, 38(10): 1475–84, Oct. 1995, Abstract only.

(List continued on next page.)

*Primary Examiner*—W. Gary Jones
*Assistant Examiner*—Diana Johannsen
(74) *Attorney, Agent, or Firm*—Sidley Austin Brown & Wood (57) ABSTRACT

Disclosed is a genetic testing method for diagnosing systemic lupus erythematosus (SLE) in a human subject. The method is related to amplifying nucleic acids from human tissue samples and analyzing for a variant allele of a gene encoding poly(ADP-ribosyl)transferase expression (PARP), which is diagnostic of SLE or indicates a genetic predisposition for developing SLE. Also disclosed are useful oligonucleotide primers, primer sets and genetic testing kits for detecting a genetic predisposition for developing SLE.

7 Claims, 1 Drawing Sheet

OTHER PUBLICATIONS

Casciola–Rosen, L., et al., "Ultraviolet light–induced keratinocyte apoptosis: a potential mechanism for the induction of skin lesions and autoantibody production in LE", *Lupus*, 6(2): 175–80, 1997.

Davidson, A., et al., "Diagnosing and Treating the Predominantly Female Problems of Systematic Autoimmune Diseases", *Medscape Womens Health*, 2(2): 6, Feb. 1997, Abstract only.

Engelstein, M., et al., "A PCR–based linkage map of human chromosome 1", *Genomics*, 15(2): 251–8, Feb. 1993, Abstract only.

Hasan, T., et al., "Photosensitivity in lupus erythematosus, UV photoprovocation results compared with history of photosensitivity and clinical findings", *Br. J. Dermatol.*, 136(5); 699–705, May 1997, Abstract only.

Herzog, H. et al., "Human nuclear NAD+ ADP–ribosyltransferase: localization of the gene on chromosome 1q41–q42 and expression of an active human enzyme in Escherichia coli", *Proc. Natl. Acad. Sci. USA*, 86(10): 3514–8, May 1989, Abstract only.

Karlson, E.W., et al., "The relationship of socioeconomic status, race, and modifiable risk factors to outcomes in patients with systemic lupus erythematosus", *Arthritis Rheum.*, 40(1): 47–56, Jan. 1997.

Korb, L.C., et al., "C1q binds directly and specifically to suface blebs of apoptotic human keratinocytes: complements deficiency and systemic lupus erythematosus revisited", *J. Immunol.*, 158(10): 4525–8, May 15, 1997, Abstract only.

Krause, I., et al., "Seasons of the year and activity of SLE and Behcet's disease", *Scand. J. Rheumatol.*, 26(6): 435–9, (1997), Abstract only.

Kupper, J.H., et al., "Detection of poly(ADP–ribose) polymerase and its reaction product poly(ADP–ribose) by immunocytochemistry", *Histochem. J.*, 28(5): 391–5, May 1996, Abstract only.

Minami, Y., et al., "Female systemtic lupus erythematosus in Miyagi Prefecture, Japan: a case–control study of dietary and reproductive factors", *Tohoku J. Exp. Med.*, 169(3): 245–52, Mar. 1993, Abstract only.

Nyberg, F. et al., "Early detection of epidermal dust–like particles in experimentally UV–induced lesions in patients with photosensitivity and lupus erythematosus", *Acta. Derm. Venereol.*, 78(3): 177–9, May 1998, Abstract only.

Sanchez–Guerrero, J. et al., "Utility of anti–SM, anti–RNP, anti–Ro/SS–A, and anti–La/SS–B (extractable nuclear antigens) detected by enzyme–linked immunosorbent assay for the diagnosis of systemic lupus erythematosus", *Arthritis Rheum.*, 39(6): 1055–61, Jun. 1996, Abstract only.

Slater, C.A., et al., "Antinuclear antibody testing. A study of clinical utility", *Arch. Intern. Med.*, 156(13): 1421–5, Jul. 8, 1996, Abstract only.

Rood, M.J., et al., "Female sex hormones at the onset of systemic lupus erythematosus affect survival", *Br. J. Rheumatol.*, 37(9): 1008–10, Sep. 1998, Abstract only.

Rozzo, S. J., et al., "Analysis of MHC class II genes in the susceptibility to lupus in New Zealand mice", *J. Immunol.*, 162(5): 2623–30, Mar. 1, 1999, Abstract only.

Sequeira, J.F., et al., "Systemic lupus erythematosus: sex hormones in male patients", *Lupus*, 2(5): 315–7, Oct. 1993, Abstract only.

Vyse, T.J., et al., "Genetic basis of systemic lupus erythematosus", *Curr. Opin. Immunol.*, 8(6): 843–51, Dec. 1996, Abstract only.

Vyse, T.J., et al., "Genetic susceptibility to systemic lupus erythematosus", *Annu. Rev. Immunol.*, 16:261–92, 1998.

Vyse, T.J., et al., "Control of multiple autoantibodies linked with a lupus nephritis susceptibility locus in New Zealand black mice", *J. Immunol.*, 158(11): 5566–74, Jun. 1, 1997, Abstract only.

Vyse, T.J., et al., "Contributions of Ea(z) and Eb(z) MHC genes to lupus susceptibility in New Zealand mice", *J. Immunol.*, 160(6): 2757–66, Mar. 15, 1998, Abstract only.

Yoshida, S. et al., "Interaction of poly(ADP–ribose) polymerase with DNA polymerase alpha", *Mol. Cell. Biochem.*, 138(1–2): 39–44, Sep. 1994, Abstract only.

Maugh II, T.H., "Team of Researchers Narrows Search for Cause of Lupus", *Metro News, Los Angeles Times*, B–8, Wednesday, Feb. 19, 1997.

Tsao, B.P., et al., "Evidence for linkage of a candidate chromosome 1 region to systemic lupus erythematosus (SLE)", *Arthritis & Rheum.*, 39: S217, 1996, Abstract only.

Tsao, B.P., et al., "The genetic basis of systemic lupus erythematosus", *Proc. Assoc. Am. Physicians*, 110(2): 113–7, Mar.–Apr. 1998.

Tsao, B.P., et al., "Genetic susceptibility to lupus nephritis", *Lupus*, 7(9): 585–90, 1998.

Tsao, B.P., et al., "PARP alleles within the linked chormosomal region are associated with systemic lupus erythematosus", *J. Clin. Invest.*, 103(8): 1135–40, Apr. 1999.

Tsao, B.P., et al., "Evidence for linkage of a candidate chromosome 1 region to human systemic lupus erythematosus", *J. Clin. Invest.*, 99(4): 725–731, Feb. 1997.

Oliver, F. J., et al., "DNA Repair '99 Poly(ADP–Ribose) Polymerase in the Cellular Response to DNA Damage, Apoptosis, and Disease", *Am. J. Hum. Genet.*, 64: 1282–1288. 1999.

Moser, K.L., et al., "Genome scan of human systemic lupus erythematosus: Evidence for linkage on chromosome 1q African–American pedigrees", *Proc. Natl. Acad. Sci. USA*, 95: 14869–14874, Dec. 1998.

Gaffney, P.M., et al., "A genome–wide search for susceptibility genes in human systemic lupus erythematosus sib–pair families", *Proc. Natl. Acad. Sci. USA*, 95: 14875–14879, Dec. 1998.

Sibley, J.T., et al., "Altered metabolism of poly(ADP–ribose) in the peripheral blood lymphocytes of patients with systemic lupus erythematosus", *Arthritis and Rheumatism*, 32(8): 1045–1049, Aug. 1989.

Haug, B.L., et al., "Altered Poly(ADP–Ribose) Metabolism in Family Members of Patients with Systemic Lupus Erythematosus", *J. Rheumatol.*, 21: 851–56, 1994.

Lee, J.S., et al., "Decreased mRNA Levels Coding for Poly(ADP–Ribose) Polymerase in Lymphocytes of Patients with SLE", *Lupus*, 3:113–116, 1994.

Loetscher, P., et al., "Poly(ADP–ribose) may signal changing metabolic conditions to the chromatin of mammalian cells", *Proc. Natl. Acad. Sci. USA*, 84(5): 1286–9, Mar. 1987, Abstract only.

Hirose, S., et al., "Mapping of a gene for hypergammaglobulinemia to the distal region on chromosome 4 in NZB mice and its contribution to systemic lupus erythematosus in (NZB x NZW) F1 mice", *Int. Immunol.*, 6(12): 1857–64, Dec. 1994, Abstract only.

Morel, L. et al., "Multiplex inheritance of component phenotypes in a murine model of lupus", *Mamm. Genome*, 10(2): 176–81, Feb. 1999, Abstract only.

Morel, L. et al., "Polygenic control of susceptibility to murine systemic lupus erythematosus", *Immunity*, 1(3): 219–29, Jun. 1994, Abstract only.

Cornillet, P. et al., "Increased freqency of the long (S) allotype of CR1 (the C3b/C4b receptor, CD35) in patients with systemic lupus erythematosus", *Clin. Exp. Immunol.*, 89(1): 22–5, Jul. 1992, Abstract only.

Kumar, A. et al., "Hind III, genomic polymorphism of the C3b receptor (CR1) in patients with SLE: low erythrocyte CR1 expression is an acquired phenomenon", *Immunol. Cell Biol.*, 73(5): 457–62, Oct. 1995, Abstract only.

Deguchi, Y. et al., "A human homeobox gene, HB24, inhibits development of CD4+ T cells and impairs thymic involution in transgenic mice", *J. Biol. Chem.*, 268(5): 3646–53, Feb. 15, 1993, Abstract only.

Raz, E. et al., "Modulation of disease activity in murine systemic lupus erythematosus by cytokine gene delivery", *Lupus*, 4(4): 286–92, Aug. 1995, Abstract only.

Slater, C.A. et al., "Antinuclear antibody testing. A study of clinical utility." *Arch Intern. Med.*, 156(13): 1421–5, Jul. 8, 1996, Abstract only.

Suarez–Almazor, M.E. et al., "Utilization and predictive value of laboratory tests in patients referred to rheumatologists by primary care physicians", *J. Rheumatol.*, 25(10); 1980–5, Oct. 1998.

Tan, E.M. et al., "The 1982 revised criteria for the classification of systemic lupus erythematosus", *Arthritis Rheum.*, 25(11): 1271–7, Nov. 1982, Abstract only.

Watson, M.L. et al., "Genetic analysis of MRL–lpr mice: relationship of the Fas apoptosis gene to disease manifestations and renal disease–modifying loci", *J. Exp. Med.*, 176(6): 1645–56, Dec. 1, 1992, Abstract only.

Kono, D.H. et al. "Lupus susceptibility loci in New Zealand Mice", *Proc. Natl. Acad. Sci. USA*, 91(21):10168–72, Oct. 11, 1994, Abstract only.

Drake, C.G. et al., "Genetic analysis of the NZB contribution to lupus–like autoimmune disease in (NZB x NZW) F1 mice", *Proc. Natl. Acad. Sci. USA*, 91(9): 4062–6, Apr. 26, 1994, Abstract only.

Kuokkanen S., "A putative vulnerability locus to multiple sclerosis maps to 5p14–p12 in a region syntenic to the murine locus Eae2", *Nat. Genet.*, 13(4): 477–80, Aug. 1996, Abstract only.

Botto, M. et al., "Homozygous C1q deficiency causes glomerulonephritis associated with multiple apoptotic bodies", *Nat. Genet.*, 19(1): 56–9, May 1998, Abstract only.

Bowness, P. et al., "Hereditary C1q deficiency and systemic lupus erythematosus", *QJM*, 87(8): 455–64, Aug. 1994, Abstract only.

Botto, M. et al., "Fc gamma RIIa polymorphism in systemic lupus erythematosus (SLE): no association with disease", *Clin. Exp. Immunol.*, 104(2): 264–8, May. 1996, Abstract only.

Botto, M., "C1q knock–out mice for the study of complement deficiency in autoimmune disease", *Exp. Clin. Immunogenet.*, 15(4): 231–4, 1998, Abstract only.

Tsao, B.P. et al., "ADPRT alleles from the chromosome 1q41–q42 linked region are associated with SLE", *Arthritis & Rheum.*, 41:580, 1998, Abstract only Fougerousse, F. et al. Nucleic Acids Res. 20(5):1116 1992.*

Ahern, H. The Scientist 9(15):20, Jul. 1995.*

Murray, J. et al. GenEmbl Accession No. G08223, Feb. 1997.*

Doggett, N.A. et al. Genomics 18:687–689, 1992.*

Delrieu, O. et al. Arthritis & Rheumatism 42(10):2197–2197, Oct. 1999.*

* cited by examiner

FIG. 1

GENETIC MARKER TEST FOR LUPUS

BACKGROUND OF THE INVENTION

Throughout this application various publications are referenced within parentheses. The disclosures of these publications in their entireties are hereby incorporated by reference in this application in order to more fully describe the state of the art to which this invention pertains.

1. The Field of the Invention

This invention relates to the medical arts. In particular, it relates to a method of detecting a genetic predisposition to systemic lupus erythematosus.

2. Discussion of the Related Art

Systemic lupus erythematosus (SLE), commonly known as lupus, is an autoimmune rheumatic disease characterized by deposition in tissues of autoantibodies and immune complexes leading to tissue injury (B. L. Kotzin, *Systemic lupus erythematosus*, Cell 85:303–06 [1996]). In contrast to autoimmune diseases such as multiple sclerosis and type 1 diabetes mellitus, SLE potentially involves multiple organ systems directly, and its clinical manifestations are diverse and variable. (Reviewed by B. L. Kotzin and J. R. O'Dell, *Systemic lupus erythematosus*, In: *Samler's Immunologic Diseases*, 5th ed., M. M. Frank et al., eds., Little Brown & Co., Boston, pp. 667–97 [1995]).

For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide. (B. L. Kotzin [1996]). The serological hallmark of SLE, and the primary diagnostic test available until now, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (GN). (B. H, Hahn and B. Tsao, Antibodies to DNA, In: *Dubois' Lupus Erythematosus*, 4th ed., D. J. Wallace and B. Hahn, eds., Lea and Febiger, Philadelphia, pp. 195–201 [1993]; Ohnishi et al., Comparison of pathogenic and nonpathogenic murine antibodies to DNA: Antigen binding ard structural characteristics, Int. Immunol. 6:817–30 [1994]). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

Mechanisms by which autoantibodies are induced remain unclear. Chromatin and/or nucleosomes, released by apoptotic cells in SLE, may become autoantigens that induce autoimmune responses, including antibodies to dsDNA. (R. W. Burlingame et al., The central role of chromatin in autoimmune responses to histones and DNA in systemic lupus erythematosus, J. Clin. Invest. 94:184–92 [1994]; C. Mohan et al., Nucleosome: a major immunogen for pathogenic autoantibody-inducing T cells of lupus, J. Exp. Med. 177:1367–81 [1993]; D. A. Bell el al., Immunogenic DNA-relatedfactors. Nucleosomes spontaneously released from normal murine lymphoid cells stimulate prolferation and immunoglobulin synthesis of normal mouse lymphocytes, J. Cin. Invest. 85:1487–96 [19909 ).

Cumulative studies suggest that interaction of multiple genes and environmental factors result in susceptibility to SLE, as is true for many multifactorial complex human diseases. (F. C. Arnett, Jr., The genetics of human lupus, In: *Dubois' Lupus Erythematosus*, 5th ed., D. J. Wallace and B. Hahn, eds., Williams and Wilkins, Baltimore, pp. 77–117 [1997]; T. J. Vyse and B. L. Kotzin, Genetic susceptibility to systemic lupus erythematosus, Ann. Rev. Immunol. 16:261–92 [1998]). Although SLE can occur at nearly any age, it primarily affects women of childbearing age; the female to male ratio is greatest (>8:1) for patients presenting between ages 15 to 50 years; incidence rates for patients and studies in certain animal models support a role for estrogens enhancing disease development, and androgens protecting against it. (B. L. Kotzin [1996]). Although rare among males, SLE may be linked in males with functional hypoandrogenism and a higher than normal estradiol/testosterone ratio. (J. F. Sequeira el al., *Systemic lupus erythematosus*: sex hormones in male patients, Lupus 2(5):315–17 [1993]).

It appears that underlying genetic factors exert the greatest influence on autoantibody production and on predisposition to SLE, as studies of populations, segregation of disease in families, and twin concordance rates have consistently demonstrated. The prevalence of SLE in the general population is approximately 15–50 in 100,000. (M. D. Hochberg, The epidemiology of *systemic lupus erythematosus*, In: *Dubois' Lupus Erythematosus*, 5th ed., D. J. Wallace and B. Hahn, eds., Williams and Wilkins, Baltimore, pp. 49–65 [1997]). The relatively high incidence (10–16%) of more than one case in a family has suggested a genetic basis for SLE. The concordance rate of SLE in monozygotic twins (24%–57%) is approximately ten times higher than the rate in dizygotic twins (2–5%). (F. C. Arnett, Jr. [1997]; M. D. Hochberg [1997]). Based on these epidemiological studies, the relative risk for siblings of SLE patients compared to the general population, As, is at least 40-fold. (See, N. Risch, Assessing the role of HLA-linked aid unlinked determinants of disease, Am. J. Hum. Genet. 40:1–14 [1987]).

The genetic basis for SLE in humans is complex, with an unknown but non-Mendelian mode of inheritance. This complexity has impeded the development of a reliable and predictive genetic test for SLE until the present invention.

Many investigators have reported that certain human MHC class II alleles (HLA-DR and/or DQ but not DP) and certain class III genes (C2, C4, TNFα and HSP70-2 alleles) confer susceptibility to SLE in most ethnic groups studied. (F. C. Arnett, Jr., The genetics of human lupus, In: *Dubois' Lupus Erythematosus*, 5th ed., D. J. Wallace and B. Hahn, eds., Williams and Wilkins, Baltimore, pp. 77–117[1997]; T. J. Vyse and B. L. Kotzin, Genetic susceptibility to systemic lupus erythemalosus, Ann. Rev. Immunol. 16:261–92 [1998]). Among the other non-MHC genes that have been associated with SLE, evidence for homozygous deficiency of Clq predisposing to SLE is particularly compelling, including the observation that 90% of such individuals have SLE and Clq knockout mice display an SLE-ike phenotype. (M. Botto et al., Homozygous Clq deficiency causes glomerulonephritis associated with multiple apoptotic bodies, Nat. Genet. 19:56–59 [1998]; P. Bowness et al., Hereditary Clq deficiency and *systemic lupus erythematosus*, Quart. J. Med. 87:455–64 [1994]).

In addition, polymorphisms in many genes encoding molecules with relevant immunological functions have been studied most frequently by the case-control approach, including T-cell receptor α and β chains, immunoglobulin allotypes, FcγRIIa, FcgRIIIa, IL-6, IL-10, Bcl-2, mannose-binding protein (or lectin), as well as deletion of specific variable gene segments of immunoglobulin genes. (F. C.

Arnett, Jr. [1997]; T. J. Vyse and B. L. Kotzin [1998], J. Wu et al., A novel polymorphism of FcγRlilA, which alters function, associates with SLE phenotype, J. Invest. Med. 45:200A [1997]; R. Mehrian et al., Synergistic effect between IL-10 and Bcl-2 genotypes in determining susceptibility to systemic lupus erythematosus, Arthritis Rheum. 41:596–602 [1998]). Mutations in nucleic acids encoding T cell receptor zeta chain have been linked to SLE in some patients. (K. Tsuzaka et al, Mutations in T cell receptor zeta chain mRNA of peripheral T cells from *systemic lupus erythematosus* patients, J. Autoimmun. 11 (5):381–85 [1998]). Some candidate genes may confer risk only to subsets of SLE patients. For example, FcγRIIA alleles (the gene encoding a 40-kD FcγR expressed on human mononuclear phagocytes and neutrophils) confer an increased risk for lupus GN in African Americans, but not in Caucasians, or persons of Afro-Caribbean or Chinese origin. (J. E. Salmon et al, FcγRIIA alleles are heritable risk factors for lupusnephritis in African-Americans, J. Clin. Invest. 97:1348–54 [1996]; M. Botto et al., FcγRIIA polymorphism in systemic lupus erythematosus [SLE], Clin. Exp. Immunol. 104:264–68 [1996]).

Elements that complicate the study of disease-causing genes in genetically complex diseases, such as human SLE, include ethnic diversity, clinical heterogeneity (and presumably genetic heterogeneity), reduced penetrance (genetic expressivity), and the effect of environment (E. S. Lander and N. J. Schork, Genetic dissection of complex traits, Science 265:2037–48 [1994]). In contrast, murine models of spontaneous lupus in inbred strains are less complex, and consequently murine models of disease susceptibility provide a more accessible route for investigating genetically-linked disease in humans. Recent success in mapping a susceptibility locus for multiple sclerosis in the 5p14-p12 region, which is syntenic to the murine locus Ea2, further supports the utility of this mouse-to-human approach. (S. Kuokkanen el al., A putative vulnerability locus to multiple sclerosis maps to 5p14-p12 in a region syntenic to the murine locus Eae2, Nature Genet. 13:477–80 [1996]).

Genetic studies of murine SLE have identified susceptibility loci in several inbred strains which spontaneously develop SLE GN. (Reviewed in A. N. Theofilopoulus, The basis of autoimmunity: Part II. Genetic predisposition, Immunology Today 15:150–58 [1995]). These studies have included genome-wide searches for evidence of linkage using backcrosses or $F_2$ intercrosses of lupus mice such as MRL/LPR, NZB/NZW and NZM/Aeg2410 (M. L. Watson et al., Genetic analysis of MRL-lpr mice: Relationship of the Fas apoptosis gene to disease manifestations and renal disease-modifying loci, J. Exp. Med. 176:1645–56 [1992]; D. H. Kono et al., Lupus susceptibility loci in New Zealand mice, Proc. Natl. Acad. Sci. USA 91; 10168–72 [1994];Drake et al., Analysis of the New Zealand Black contribution to lupuis-like renal disease: multiple genes that operate in athresholdmanner, J. Immunol. 154:241–47 [1995]; Drake et al., Genetic analysis of the NZB contribution to lupus-like autoimmune disease in [NZB×NZW]$F^1$ mice, Proc. Natl. Acad. Sci. USA 91:4062–66 [1994]; S. Hirose et al., Mapping of a gene for hypergammaglobulinemia to the distal region chromosome 4 in NZB mice and its contribution to systemic lupus erythematosus in [MVZB×NZW]F, mice, Internat. Immmunol. 12:1857–64 [1994]; L. Morel et al., Polygenic control of susceptibility to murine SLE, Immunity 1:219–229 [1994]).

Four genomic intervals strongly linked to GN in mice derived from different parental strains have been identified in multiple studies at loci on chromosomes 1, 4, 7, and 17. The distal end of mouse chromosome 1 was shown to predispose to specific manifestations of SLE, including GN, IgG anti-chromatin antibodies, and splenomegaly. (D. H. Kono et al.[1994]; Drake et al. [1995]; L. Morel et al. [1994]).

There is evidence for a corresponding genetic linkage in human SLE. Using the identified murine susceptibility loci (the overlapping SLE/Nba2/Lbw7) as a guide, Tsao et al. examined seven markers located on a syntenic human chromosomal lq31-q42 region, corresponding to the telomeric end of mouse chromosome 1, the latter being the region where contributions to specific manifestations of murine lupus, including glomerulonephritis and IgG anti-chromatin, have been mapped. (B. Tsao et al., Evidence for linkage of a candidate chromosome 1 region to human *systemic lupus erythematosus*, J. Clin. Invest. 99:725–731 [1997]). The seven markers were examined in 52 affected human sibpairs from Caucasian, Asian and African-American families. Five markers located in a 15 cM region of human chromosome lq41-q42 showed evidence for linkage excessive by the allele sharing method (B. Tsao et al. [1997]; B. Tsao et al., The genetic basis of systemic lupus erythematosus, Proc. Assoc. Am. Physicians 110(2): 113–17 [Review March–April 1998]). Subsequently, an independent sample of 105 SLE-affected sibpairs also supported linkage of the lq41-q42 region with SLE. (P. M. Gaffihey et al., A genome-wide search for susceptibility genes in human systemic lupus erythematosus sib-pair families, Proc. Natl. Acad. Sci. USA [in press]).

The distance (>60 cM) between the lq41-q42 region and the FcγRIIa gene (lq23) make it unlikely that this gene could account for the observed linkage between the lq41-q42 region and SLE. A polymorphism for low expression of CR1 (complement receptor one, previously C3b/C4b receptor) has been suggested to be a risk factor for SLE (P. Cornillet et al., Increased frequency of the long (S) allotype of CR1 (the C3b/C4b receptor, CD35) in patients with systemic lupus erythematosus, Clin. Exp. Immunol. 89:22–25 [1992]), although a later study suggests that low CR1 expression is acquired. (A Kunar et al., HindIII genomic polymorphism of the C3b receptor (CR1 in patients with SLE: low erythrocyte CR1 expression in acquired phenomenon, Immunol. Cell Biol. 73:457–62 [1995]). However, the CR1 gene maps to chromosome lq32, and linkage disequilibrium at the lq41-42 region, but not at the lq31–32 region, make CR1 an unlikely candidate as a susceptibility gene for SLE. (B. Tsao et al. 1997]).

Within the human chromosomal lq41-q42 region, there are three candidate genes for linkage with an SLE phenotype. One of these, HLX1, is expressed in hematopoietic progenitors and activated lymphocytes and encodes a bomeo box protein which may regulate the development of CD4$^+$ T-cells. (Y. Deguchi et al., A human homeobox gene, HB24, inhibits development of CD4$^+$ T cells and impairs thymic involution in transgenic mice, J. Biol. Chem. 268:3646–53 [1993]). Another, TGFB2 (transforming growth factor beta-2) can suppress I1–2 dependent T-cell growth (R. Demartin et al., Complementary DNA for human glioblastoma-derived T cell suppressor factor, a novel member of the transforming growth factor-beta gene family, EMBO J. 6:3673–77 [1987]), and administration of a TGFβCDNA expression vector to MRL/lpr mice decreases serum IgG anti-chromatin and delays the onset of SLE. (E. Raz et al., Modulation of disease activity in murine systemic lupus erythematosus by cytokine gene delivery, Lupus 4:286). However, TGFB2 is not expressed in hematopoietic cells, and such expression is believed to be an essential link in the etiology of SLE.

The third candidate gene, PARP, sometimes referred to as ADPRT (ADP-ribosyltransferase ene), is induced by DNA damage and plays a role in cellular repair (P. Loetscher et al., Poly(ADP-ribose) may signal changing metabolic conditions lo the chromatin of mammalian cells, Proc. Natl. Acad. Sci. USA 84:1286–89 [1987]). Haug et al. reported that SLE patients and their family members have decreased poly (ADP-ribose) metabolism. (B. L. Haug et al., Altered poly (ADP-ribose) metabolism in family members of patients with *systemic lupus erythematosus*, J. Rheum. 21:851–56 [1994]), which is evidence that PARP is linked to SLE.

The PARP gene encodes poly(ADP-ribosyl)transferase, also known as poly(ADP-ribosyl)polymerase, which is a zinc-finger DNA-binding protein that repairs DNA damage and is specifically cleaved during apoptosis. (B. Tsao et al., ADPRT alleles from the chromosome Iq41-q42 linked region are associated with SLE, Arthritis & Rheumatism 41(9)(Suppl.):283 [Abstract, September 1998]). In their abstract, Tsao et al. reported that none of the tested alleles of HLX1 showed evidence for association with SLE phenotypes in a family-based linkage test applied to 124 families. However, a polymorphism within the PARP region was associated with SLE phenotype. This polymorphism was reported to be a dinucleotide repeat in the PARP promoter region.

There has been a need for a rapid and accurate genetic test for SLE. Previously available diagnostic tests for SLE are limited in their diagnostic effectiveness. Rheumatoid factors (RF), antinuclear antibodies (ANA), and erythrocyte sedimentation rate (ESR) are among the most frequently used tests for the diagnosis and investigation of connective tissue disease, including SLE. However, positive predictive values for these diagnostic tests are reported to be low as to a diagnosis of SLE, albeit they may be more predictive for a subject having other clinical SLE symptoms from among the 11 revised SLE criteria of the American College of Rheumatology (ACR), such as a typical malar or discoid rash, photosensitivity, oral ulcers, arthritis, serositis, or disorders of blood, kidney or nervous system. E. M Tan et al., The 1982 revised criteria for the classification of systemic lupus erythematosus [SLE], Arthritis Rheum. 25:1271–77 [1982]; M. E. Suarez-Almazor et al., Utilization and predictive value of laboratory tests in patients referred to rheumatologists by primary care physicians, J. Rheumatol. 25(l0);1980–85 [1998]; C. A. Slater et al., Antinuclear antibody testing. A study of clinical utility, Arch. Intern. Med. 156(13):1421–25 [1996]). The diagnostic utility of ELISA assay for the presence of anti-extractable nuclear antigen (anti-ENA) antibodies is limited to those patients that also test positive for both ANA and anti-dsDNA antibodies. (J. Sanchez-Guerrero et al., Utility of antism, anti-RNP, anti-Ro/SS-A, and anti—La/SS-B [extractable nuclear antigens] detected by enzyme-linked immunosorbent assa for the diagnosis of *systemic lupus erythematosus*, Arthritis Rheum. 39(6):1055–61 [1996]).

Unfortunately, a patient's presentation of clinical symptoms in SLE may be vague or idiopathic, easily mistaken for another disorder. For example, uncommon clinical manifestations associated with underlying SLE may include, acute pancreatitis, pure red cell aplasia, cystitis of the urinary tract, antiphospholipid antibody syndrome, or neurological complications of normal pressure hydrocephalus. (K. P. Leong and M. L. Boey, *Systemic lupus erythematosus* [SLE] presenting as acute pancreatitis—a case report, Singapore Med. J. 37(3):323–24 [1996]; M. H. Tsai et al., Systemic lupus erythematosus with pure red cell aplasia: a case report, Chung Hua I Hsueh Tsa Chih [Taipei] 52(4):265–68 [1993]; Y. Nakauchi et al., *Systemic lupus erythematosus* relapse with *lupus cystitis*, Clin. Exp. Rheumatol. 13(5):645–48 [1995]; P. R. Mortifee et al., Communicating hydrocephalus in *systemic lupus erythematosus* with antiphospholipid antibody syndrome, J. Rheumatol. 19(8):1299–1302 [1992]; H. Y. You et al., Normal pressure hydrocephalus in apatient with *systemic lupus erythematosus*: a case report, Chung Hua I Hsueh Tsa Chih [Taipei] 61(9):551–55 [1998]; M. D. Uhl el al., Normal pressure hydrocephalus in a patient with *systemic lupus erythematosus*, J. Rheumatol. 17(2):1689–91 [1990]).

Consequently, a genetic testing method for SLE has been needed that can be used in conjunction with other diagnostic tests for SLE. This, and other advantages described herein, the present invention provides.

SUMMARY OF THE INVENTION

The present invention relates to a genetic testing method for diagnosing the autoimmune disease systemic lupus erythematosus in a human subject. In particular, the claimed invention is directed to amplifying nucleic acids from a tissue sample of a human subject, analyzing the amplification products for the presence of a variant allele in PARP, the gene which encodes for expression of poly(ADP-ribosyl) transferase. A variant allele of PARP is diagnostic of SLE in a human subject having symptoms of SLE or indicates a genetic predisposition for SLE in a subject who does not present SLE symptoms. The methods of the present invention provide a hitherto unavailable genetic test for susceptibility to this potentially life-threatening disease.

The method of the present invention relates to amplification of the nucleic acids in a human tissue sample using oligonucleotide primers specific for a nucleic acid sequence derived from the genomic sequence of human chromosome lq41-q42 between microsatellite markers D1S2860 and D1S213. The present invention also relates to a genetic testing method for diagnosing SLE by amplifying nucleic acids having a variant allele in a PARP promoter region, for example, the 85 base pair or 97 base pair alleles, which are associated, respectively, with increased or decreased genetic susceptibility to SLE in subjects from diverse ethnic origins.

Another feature of the present invention are oligonucleotide primer sequences used for detecting a genetic susceptibility to SLE, a primer set with which to practice the present method, and a genetic testing kit comprising these primers or the primer set.

The present invention provides a rapid and accurate genetic test for SLE. It can be applied diagnostically in conjunction with other available diagnostic tests in suspected cases of SLE. The methods, primers, and genetic testing kits of the present invention can also be applied so that a person without any of the symptoms of SLE, but who is found to possess a genetic predisposition for SLE, can be treated to minimize his or her exposure to environmental risk factors in order to prevent the development of SLE.

These and other advantages and features of the present invention will be described more fully in a detailed description of the preferred embodiments which follows.

DETAILED DESCRIPTION OF THE PREFERRED EMBODIMENTS

The present invention relates to a genetic testing method for diagnosing systemic lupus erythematosus in a human subject. The present invention provides a hitherto unavailable genetic testing method for susceptibility to this potentially life-threatening disease. In particular, the claimed invention is directed to amplifying nucleic acids from a tissue sample of a human subject, analyzing the amplification products for the presence of a variant allele in PARP, a gene encoding for expression of poly(ADP-ribosyl) transferase. A variant allele of PARP is diagnostic of SLE in a subject having clinical SEE symptoms or indicates a genetic predisposition for developing SLE in a subject who does not present SLE symptoms.

A PARP gene, for the purposes of the present invention, is a gene that encodes poly(ADP-ribosyl) transferase. Poly (ADP-ribosyl) transferase (E.C. 2.4.2.30) functions in the maintenance of genomic integrity; it is the only enzyme known to synthesizes ADP-ribose polymers from nicotinamide adenine dinucleotide ($NAD^+$) and is activated in response to DNA strand breaks. (W. M. Shieh et al., Poly (ADP-ribosyl)polymerase null mouse cells synthesize ADP-ribose polymers, J. Biol. Chem. 273(46):30069–72 [1998]). Poly(ADP-ribosyl) transferase enzyme has been shown to stimulate DNA polymerase a by physical association and may form a complex with DNA polymerase a in vivo. (C. M. Simbulan et al., Poly(ADP-ribose)polymerase stimulates DNA polymerase alpha by physical association, J. Biol. Chem. 268(1):93–99 [1993]). Activation of poly(ADP-ribosyl) transferase requires both the DNA-binding capacity of the DNA-binding domain ("zinc fingers") and the ability to maintain a conformation of the DNA-binding domain that can transfer an "activation signal" to the catalytic domain of the enzyme. (C. Trucco et al., Mutations in the amino-terminal domain of the human poly(ADP-ribose)polymerase that affect its catalytic activity but not its DNA-binding capacity, FEBS Lett. 399(3):313–16 [1996]).

The important physiologic function of poly(ADP-ribosyl) transferase has been extensively studied by using specific inhibitors (3-aminobenzamide, 3-methoxybenzamide, or antisense RNA) and by studies of knockout mice. (P. A. Jeggo, DNA repair: PARP-another guardian angel?, Current Biol. 8:R49-R5 [1998]). Cumulative data have shown that the absence of poly(ADP-ribosyl) transferase activity results in elevated spontaneous genetic rearrangements and hypersensitive responses to DNA damage, implying a substantial role for poly(ADP-ribosyl) transferase in maintaining genomic stability. Although no gross defects in apoptosis are found in PARP knockout mice, splenocytes of these mice display a more rapid apoptotic response to an alkylating agent. Cell lines with disrupted PARP expression show insensitivity to apoptotic signals. (C. M. Simbulan-Rosenthal el al., Transient poly(ADP-ribosyl)ation of nuclear proteins and role of poly(ADP-ribose)polymerase in the early stages of apoptosis, J. Biol. Chem. 273:13703–12 [1998]). While PARP has a regulatory role in induced apoptosis, impaired apoptosis is less detectable in whole animals than in cell lines, probably because of other compensatory routes within the organism.

The present invention is not committed to any particular mechanism by which altered PARP expression or various PARP alleles may produce symptoms of, or susceptibility to, SLE. Howvever, it is hypothesized that the 85 bp allele of PARP, or other variant alleles of PARP, confers defective DNA repair and abnormal apoptosis, and thus predisposes to SLE. Further support for this hypothesis of the direct involvement of PARP gene product in SLE predisposition includes a lower than normal range of poly(ADP-ribosyl) transferase activity in SLE patients, an intermediate range of activity in unaffected family members of SLE patients, and decreased levels of PARP mRNA transcripts in SLE patients. (S. L. Oei et al. [1997]; P. A. Jeggo [1998]). The specific examples provided herein demonstrate that PARP is a SLE susceptibility gene.

Human PARP is located on chromosome 1 at locus lq41-q42. (H. Herzog et al., Human nuclear $NAD^+$ ADP-ribosyltransferase: localization of the gene on chromosome lq4-q42 and expression of an active human enzyme in *Escherichia coli*, Proc. Natl. Acad. Sci. USA 86(10):3514–18 [1989]). More specifically, the PARP gene region is flanked by microsatellite markers D1S2860 and D1S213 (See FIG. 1)(C. Dib et al., A comprehensive genetic map of the human genome based on 5,264 microsatellites, Nature 380(6570):152–54 [1996]). The PARP gene is 43 kb in length and is split into 23 exons. (B. Auer et al., Human nuclear $NAD^+$ ADP-ribosyltransferase: organization of the gene, DNA 8(8):575–80 [1989]). Each of the four met al coordinating sites forming the two "zinc fingers" of the poly(ADP-ribosyl) transferase DNA-binding domain is encoded separately; the automodification and $NAD^+$-binding domains are encoded by four and twelve exons, respectively. Nucleotide sequences of the entire human PARP genomic region are known, including nucleotide sequences defining regulatory and open reading frame regions. (H. Suzuki et al., Molecular cloning of cDNA for human poly(ADP-ribose)polymerase and expression of its gene during HL-60 cell differentiation, Biochem. Biophys. Res Commun. 146(2):403–09 [1987]; B. W. Cherney el al., cDNA sequence, protein structure, and chromosomal location of the human gene for poly(ADP-ribose)polymerase, Proc. Natl. Acad. Sci. USA 84(23):8370–74 [1987]; T. Ogura et al., Characterization of a putative promoter region of the human poly(ADP-ribose)polymerase gene: structural similarity to that of the DNA polymerase beta gene, Biochem. Biophys. Res. Commun. 167(2):701–10 [1990]; Y. Yokoyama et al., Humanpoly(ADP-fibose)polymerasegene. Cloning of the promoter region, Eur. J. Biochem. 194(2):521–26 [1990]). Several restriction fragment length polymorphisms of the PARP gene are also known. (B. W. Cherney et al. [1987]).

Variant alleles of the PARP gene include mutations or polymorphisms of any class. Many variant alleles of PARP are known. These include several single point mutations that cause a loss of poly(ADP-ribosyl) transferase catalytic activity. (C. Trucco et al., [1996]). But for purposes of the present invention, variant alleles of PARP are not limited to such single nucleotide polymorphisms (SNPs). Also included among variant alleles of PARP are deletion mutations, insertion mutations, inversions, translocations, transitions, tranversions, or repeats. An example, is the dinucleotide CA repeat that occurs in the 85 bp allele of a PARP promoter region; this dinucleotide repeat is located 906 bp upstream from the transcription start site, near the binding site of the transcription factor Ying Yang 1. (S. L. Oei et al., Interaction of the transcription factor YY1 with human poly(ADP-ribosyl)tranferase, Biochim. Biophys. Res. Comm. 240:108–11 [1997]).

Variant alleles of a PARP gene may be of any nucleotide sequence defining an open reading frame, or part thereof, that encodes any subunit of the catalytic or automodification domain, or the DNA-binding domain, or the $NAD^+$-binding domain of poly(ADP-ribosyl) transferase, or of any nucleotide sequence, or part thereof, defining a regulatory region of a PARP gene. A PARP regulatory region may include, but is not limited to, a promoter region, an enhancer, a termination sequence, or any other nucleotide sequence, or part thereof, that regulates the transcription of poly(ADP-ribosyl) transferase protein. Any mutation or polymorphism in a PARP gene that results in a loss of PARP expression or a decrease in poly(ADP-ribosyl) transferase functional activity relative to a normal activity range, or which could do so if it were not masked by the presence in vivo of a fully functional PARP allele or by another compensatory physiologic mechanism, are contemplated by the present invention.

Any human tissue containing nucleic acids may be sampled and collected for the purpose of practicing the methods of the present invention. A most preferred and convenient tissue for collecting is blood. "Collecting a tissue sample" encompasses in vitro harvest of cultured human cells derived from a subject's tissue or any means of in vivo sampling directly from a subject, for example, by blood draw, spinal tap, tissue smear or tissue biopsy. Tissue samples may be stored before analysis by well known storage means that will preserve a sample's nucleic acids in an analyzable condition, such as quick freezing, or a controlled freezing regime, in the presence of a cryoprotectant, for example, dimethyl sulfoxide (DMSO), glycerol, or propanediol-sucrose. Tissue samples may also be pooled before or after storage for purposes of amplifying them for analysis.

For purposes of the present invention "amplifying nucleic acids" from a tissue sample of a subject "to obtain amplification products" encompasses any conventional means of amassing sufficient nucleic acid material for analysis. This includes, but is not limited to, amplification by conventional polymerase chain reaction (PCR) methods. Alternatively, the practitioner can amplify the human subject's nucleic acids by in vitro cell culture and harvest of the subject's cultured cells, or by multiple sampling from the subject's tissues in vivo and pooling of multiple tissue samples from a subject. Nucleic acids thus "amplified," if they comprise a PARP gene or a part thereof, are "amplification products" for purposes of the present invention.

In a most preferred embodiment of the present method, PCR is used for amplifying the subject's nucleic acids, particularly from a PARP region. If PCR is used, any combination of oligonucleotide primers that will amplify nucleic acid sequences of a PARP region, or parts thereof, can be employed. Useful primer sequences are readily available, for example, from the GenBank database. Most preferably, amplification of the subject's nucleic acids can be achieved using oligonucleotide primers comprising a 5' (forward) primer sequence GAT TCC CCA TCT CTC TTT CTT T (SEQ. ID. NO.:1) or a 3' (reverse) primer sequence AAA TTG TGG TAA TGA CTG CA (SEQ. ID. NO.:2), or a fragment of either of these at least 18 nucleotides long.

A primer set, of the present invention, for detecting in a human subject a genetic susceptibility to SLE, functions to initiate nucleic acid synthesis in PCR from both the 5' and 3' ends of a nucleic acid template comprising a PARP region or part thereof The primer set of the present invention comprises any two suitable oligonucleotide primers of the present invention as described above. In a most preferred embodiment, a primer set of the present invention comprises primers having (SEQ. ID. NOS.:1 and 2), or fragments thereof each at least 18 nucleotides long.

A genetic testing kit of the present invention, for detecting in a human subject a genetic susceptibility to SLE, is a ready assemblage of materials for facilitating amplifying nucleic acids from a human subject comprising PARP nucleotide sequences and/or analyzing PARP-derived amplification products. A genetic testing kit of the present invention comprises at least one oligonucleotide primer of the present invention and preferably comprises a primer set of the present invention, together with instructions for the practice of the methods of the present invention. The materials or components assembled in the present genetic testing kits can be provided to the practitioner stored in any convenient and suitable ways that preserve their operability and utility. For example the components can be in dissolved, dehydrated, or lyophilized form; they can be provided at room, refrigerated or frozen temperatures.

A most preferred embodiment of the genetic testing kit of the present invention comprises a primer set having (SEQ. ID. NOS.:1 and 2), or fragments thereof each at least 18 nucleotides long, together with instructions for practicing the present method.

A preferred embodiment of the genetic testing kit of the present invention can incorporate an array of oligonucleotide primers specific for SNPs in human PARP, preassembled in a "DNA chip" (or "gene chip") configuration for facilitating the amplifying of nucleic acids and the analyzing of amplification products. (E.g., J. G. Hacia et aL, Enhanced high density oligonucleotide array-based sequence analysis using modified nucleoside triphosphates, Nucleic Acids Res. 26(2):4975–82 [1998]; R. W. Wallace, DNA on a chip: serving up the genome for diagnostics and research, Mol. Med. Today 3(9):384–89 [1997]; T. Pastinen et al., Minisequencing: a specific tool for DNA analysis and diagnostics on oligonucleotide arrays, Genome Res. 7(6):606–[1997]; M. T. Cronin et al., Cystic fibrosis mutation detection by hybridization to light-generated DNA probe arrays, Hum. Mutat. 7(3):244–55 [1996]; A. C. Pease et al., Light-generated oligonucleotide arrays for rapid DNA sequence analysis, Proc. Natl. Acad. Sci. USA 91(11):5022–26 [1994]; E. M. Southern et al., Arrays of complementary oligonucleotides for analyzing the hybridisation behaviour of nucleic acids, Nucleic Acids Res. 22(8):1368–73 [1994]).

In a preferred embodiment of the method of the present invention, nucleotide sequencing of PARP can be used to analyze the amplification products of the nucleic acids in a human subject's tissue sample to detect a variant allele in a PARP gene. A variant allele of PARP can be detected by any nucleotide sequencing means, for example conventional dideoxy sequencing or preferably by using a commercially available automated sequencer, then by comparing the subject's nucleotide sequences to other known human PARP sequences available in genomic sequence databases, such as GenBank.

In a most preferred embodiment of the present method that employs nucleotide sequencing, sequencing of PARP maybe accomplished by using fluorescence-based single strand conformation polymorphism analysis (SSCP), a routine and reliable means of identifying point mutations, small insertions or deletions. (J. S. Ellison, Fluorescence-based mutation detection. Single-strand conformation polymorphism analysis [F-SSCP], MoL Biotechnol. 5(l):17–31 [1996]; H. Iwahana et al., Multiple fluorescence-based PCR-SSCP analysis using internal fluorescent labeling of PCR products, Biotechniques 21(3):510–14, 516–19 [1996]; R. Makino et al., F-SSCP: fluorescence-based polymerase chain reaction-single-strand conformation polymorphism [PCR-SSCP], PCR Methods Appl. 2(1):10–13 [1992]). An automated system may be used, such as an Applied Biosystems DNA sequencer, equipped with GENESCAN 672, Genetyper, or another appropriate analytical software package.

Optionally, high throughput analysis is achieved by PCR multiplexing techniques well known in the art. (E.g., Z. Lin et al., Multiplex genotype determination at a large number of gene loci, Proc. Natl. Acad. Sci. USA 93(6):2582–87 [1996]).

In another preferred embodiment of the present method, nucleotide sequencing is unnecessary for analyzing the amplification products. For example, heteroduplex analysis on high resolution gel matrices can be employed by the skilled practitioner to detect even single nucleotide polymorphisms. (M. T. Hauser et al., Generation of co-dominant PCR-based markers by duplex analysis on high resolution gels, Plant. J. 16(1):117–25 [1998]). The PCR/OLA procedure can be used for analyzing amplification products to detect SNPs in PARP. (B.R. Glick and J. J. Pasternak, *Molecular Biotechnology: Principles and Applications of Recombinant DNA*, ASM Press, Washington, D.C., pp. 197–200 [1994]). Conformation-sensitive gel electrophoresis of amplification products can also be employed as a means of analysis by the skilled artisan in practicing the methods of the present invention. (A. Markoff et al., Comparison of conformation-sensitive gel electrophoresis and single strand conformation polymorphism analysis for detection of mutations in the BRCA1 gene using optimized conformation analysis protocols, Eur. J. Genet. 6(2):145–50 [1998]).

A skilled practitioner will know that electrophoresis for analyzing amplification products is done rapidly and with high sensitivity by using any of various methods of conventional slab or capillary electrophoresis, with which the practitioner can optionally choose to employ any facilitating means of nucleic acid fragment detection, including, but not limited to, the use of radionuclides, biotin, UV-absorbance or laser-induced fluorescence. (K. Kepamnik el al., Fast detection of a (CA)18 microsatellite repeat in the Ig E receptor gene by capillary electrophoresis with laser-induced fluorescence detection, Electrophoresis 19(2);249–55 [1998]; H. Inoue el al., Enhanced separation of DNA sequencing products by capillary electrophoresis using a stepwise gradient of electric field strength, J. Chromatogr. A. 802(l):179–84 [1998]; N. J. Dovichi, DNA sequencing by capillary electrophoresis, Electrophoresis 18(12–13):2393–99 [1997]; H. Arakawa et al., Analysis of single-strand conformation polymorphisms by capillary electrophoresis with laser induced fluorescence detection, J. Pharm. Biomed. Anal. 15(9–10):1537–44 [1997]; Y. Baba, Analysis of disease-causing genes and DNA-based drugs by capillary electrophoresis. Towards DNA diagnosis and gene therapy for human diseases, J. Chromatgr B. Biomed. Appl.687(2):271–302 [1996]; K. C. Chan et al., High-speed electrophoretic separation of DNA fragments using a short capillary, J. Chromatogr B. Biomed. Sci. Appl. 695(1):13–15 [1997]).

For example, in a most preferred embodiment using a primer set containing SEQ. ID. NOS.:1 and 2 to amplify the nucleic acids, the presence of an 85 bp fragment (the 85 bp allele) is associated with a diagnosis of SLE or an increased genetic susceptibility to developing SLE in subjects of diverse ethnic origins. (See Table 2). Another example is a 97 bp fragment, product of PCR amplification using the same primer set, which indicates the 97 bp allele and is associated with decreased genetic susceptibility to SLE. Consequently, the absence of a 97 bp fragment indicates an increased genetic predisposition to develop SLE.

Any of diverse fluorescent dyes are optionally used to label primers or amplification products for ease of analysis, including but not limited to, SYBR Green I, YO-PRO-1, thiazole orange, Hex(i.e., 6-carboxy-2',4',7',4,7-hexachlorofluoroscein), FAM (i.e., 6-carboxyfluorescein), or TET (i.e., 4,7,2',7'-tetrachloro-6-carboxyfluoroscein). (E.g., J. Skeidsvoll and P. M. Ueland, Analysis of double-stranded DNA by capillary electrophoresis with laser-induced fluorescence detection using the monomeric de SYBR green I, Anal. Biochem. 231(20):359–65 [1995]; H. Iwahana et al., Multiple fluorescence-based PCR-SSCP analysis using internal fluorescent labeling of PCR products, Biotechniques 21(30:510–14, 516–19 [1996]).

Analyzing the amplification products can also be done by means of restricting the amplification products with one or more restriction enzymes, followed by separation of the resulting fragments and analysis of fragment length or differential fragment migration in denaturing high-performance liquid chromatography (DHPLC) or gel electrophoresis, as above, including restriction-capillary electrophoresis. For example, this may be achieved by techniques known in the art, such as PCR-restriction fragment-SSCP, which can detect single base substitutions, deletions or insertions. (M. Tawata el al, A mass screening device of genome by polymerase chain reaction-restriction fragment-single strand conformation polymorphism analysis, Genet. Anal. 12(3–4): 125–27 [1996]; H. H. Lee et al., Mutational analysis by a combined application of the multiple restriction fragment-single strand conformation polymorphism and the direct linear amplification DNA sequencing protocols, Anal. Biochem. 205(2);289–93 [1992]).

"Genetic predisposition" or "susceptibility" to SLE, or to develop SLE, means that a human subject having such a predisposition or susceptibility possesses an hereditary inclination or tendency to develop SLE. This does not mean that such a person will actually develop SLE at any time, merely that he or she has a greater likelihood of developing SLE compared to the general population of individuals that is not homozygous or heterozygous for a variant allele of a PARP gene or does not possess a PARP genotype or polymorphism associated with increased SLE risk.

The present invention provides a rapid and accurate genetic test for predicting susceptibility to SLE. It can be applied diagnostically in conjunction with other diagnostic tests in suspected cases of SLE to confirm a diagnosis of SLE. Previously available diagnostic tests for SLE are limited in their diagnostic effectiveness. Therefore, the methods, primers, primer sets, and genetic testing kits of the present invention provide a useful genetic test for SLE that significantly enhances the existing diagnostic armamentarium for SLE.

In addition, it is contemplated that the genetic testing methods, oligonucleotide primers, primer sets, or genetic testing kits of the present invention can be used therapeutically to detect and treat SLE patients with specific variant alleles of PARP. These variant alleles can be targeted for gene therapy directed at repairing malfunctional PARP alleles or they may suggest specific chemotherapy directed to enhancing endogenous poly(ADP-ribosyl)transferase activity or may be directed to other metabolic targets in biochemical pathways mediated by poly(ADP-ribosyl) transferase activity.

The methods, primers, primer sets, and genetic testing kits of the present invention are superior to previously available diagnostic tools for SLE, because the present invention can be applied so that a person not presenting symptoms of SLE, but who is found to possess a genetic predisposition for developing SLE, can be treated prophylactically or can make lifestyle changes to minimize his or her exposure to environmental risk factors in order to prevent the development of SLE. A person seeking genetic testing for this purpose is likely to be one with a known family history of SLE, but the genetic testing methods of the present invention are equally applicable to healthy individuals without any known family history of SLE.

The prophylactic value of genetic testing for a genetic predisposition for developing SLE can be related to a variety of environmental and physiological risk factors. For example, exposure to sunlight is a risk factor for precipitating SLE. (I. Krause et al., Seasons of the year and activity of SLE and Behcet's disease, Scand. J. Rheumatol. 26(6):435–391997]). The ultraviolet radiation in sunlight may cause damage to nuclear DNA in skin cells, resulting in apoptosis in keratinocytes, that may lead to SLE. (L. Casciola-Rosen and A. Rosen, Ultraviolet light-induced keratinocyte apoptosis: a potential mechanismfor the induction of skin lesions and autoantibody production in LE, Lupus 6(2):175–80 [1997]; F. Nyberg et al., Early detection of epidermal dust-like particles in experimentally UV-induced lesions in patients with photosensitivity and lupus erythematosus, Acta Derm. Venereol. 78(3):177–79 [1998]; T. Hasan et al., Photosensitivity in lupus erythematosus, UV photoprovocation results compared with history of photosensitivity and clinical findings, Br. J. Dermatol. 136(5):699–705 [1997]; L. C. Korb and J. M. Ahearn, Clq binds directly and specifically to surface blebs of apoptotic human keratinocytes: complement deficiency andsystemic lupus erythematosus revisited, J. Immunol. 158 (10):4525–28 [1997]). Persons who are found, through the use of methods, primers, primer sets, or genetic testing kits of the present invention, to have a predisposition for developing SLE can be advised of their particular need to minimize or avoid exposure to sunlight in order to lower SLE risk.

Also, estrogen exposure, another environmental risk factor for SLE (B. L. Kotzin [1996]), can be minimized for menopausal women who are found to have a genetic predisposition to develop SLE. Women with naturally or surgically induced menopause commonly receive estrogen replacement therapy to relieve the symptoms of ovarian hormone deficiency, including vasomoter instability and osteoporosis. Menopausal women with a known genetic predisposition to develop SLE, as detected by the methods of the present invention, can avoid standard estrogen replacement therapy, perhaps in favor of alternative hormone replacement therapies, for example, various hormone replacement combinations or alternative androgen replacement therapies known in the art. Thus, information, provided by practicing the present invention, that a genetic predisposition to develop SLE exists in a particular woman, can help that women minimize or avoid estrogen exposure in order to lower SLE risk.

At least in some Asian populations, a history of menstrual irregularity is reported to be a risk factor for SLE. (Y. Minami et al., Female *systemic lupus erythematosus* in Miyagi Prefecture, Japan: a case-control study of dietary and reproductive factors, Tohoku J. Exp. Med. 169(3):245–52 [1993]). By using the methods of the present invention to find a genetic predisposition for developing SLE, a more informed decision can be made whether to prescribe a premenopausal woman with both this risk factor, and a predisposition for SLE, appropriate hormonal therapy to regularize her period.

Similarly, because frequent intake of fatty meat, such as beef or pork, is associated with increased SLE risk, at least in some populations (Y. Minami et al.[1993]), knowledge that a particular woman has a genetic predisposition to develop SLE, can inform the practitioner to prescribe a preventative change in diet for that woman.

Also, results obtained through practicing the methods of the present invention can be used in genetic counseling to provide useful information to persons considering their reproductive options. A couple in which one or both of the partners is found to be homozygous or heterozygous for a variant allele of PARP, such as, but not limited to, the 85 bp allele of the PARP promoter region, can consider this fact in making informed reproductive choices with respect to SLE risk affecting their future offspring. For example, as determined in the detailed examples below, the risk of developing SLE with one 85 bp allele compared to having none is 2.3 while it is 4.0 with two 85 bp alleles. Such information can be factored by those skilled in the art of genetic counseling, when calculating the SLE risk for offspring.

The foregoing applications for the methods, oligonucleotide primers, primer sets, and genetic testing kits of the present invention are illustrative and by no means exhaustive. The invention will now be described in greater detail by reference to the following non-limiting examples.

EXAMPLES

Susceptibility to SLE is Linked to PARP Alleles.

Tsao et al. [1997] had analyzed, for linkage to SLE, 7 microsatellite markers present on the human chromosomal region (lq31-q42) corresponding to the telomeric end of mouse chromosome 1, the latter being the region where contributions to specific manifestations of murine lupus, including glomerulonephritis and IgG anti-chromatin. A linkage analysis of 51 sibpairs (from three ethnic groups) fulfilling 1982 American College of Rheumatology criteria for SLE showed an increased sharing of markers and haplotypes when compared to the expected random distribution (p<0.01 by a goodness-of-fit $\chi^2$). Separate analyses of these 7 markers, comparing the mean marker sharing of each to the expected value of 0.50, resulted in no evidence for linkage with the two markers present on lq31-q32 while the five markers located at lq41-q42 showed significantly increased marker sharing (p=0.0005–0.08). Also, the quantitative trait, IgG anti-chromatin, showed linkage to one of the five markers (p=0.04) and the combined marker haplotype (p<0.06), evidence that the phenotypic consequences of this susceptibility locus are conserved between mice and humans.

Within the lq41-q42 human chromosomal region, there are no recognized immunologic candidate genes to account for these results. Therefore, the lq41-q42 region was examined for SLE susceptibility gene(s), as detailed in the following examples.

Example 1

Human Subjects:

This study was approved by the Human Subject protection Committee of the University of California, Los Angeles (UCLA). These families were recruited at UCLA, and at other collaborating sites including the University of Texas, Houston (FCA; the Zentralkrankenhaus Reinkenheide in Bremerhaven, Germany (KH), and Ottawa General Hospital in Canada (RG). Simplex families were mainly recruited through UCLA rheumatologists to include SLE patients, their parents, and other sibs if available. Medical records for SLE patients were either reviewed by UCLA rheumatologists or were provided by the patients' rheumatologists in the form of completed checklists, and the checklist information was then entered into the UCLA database. This database was used for classification of patients as SLE (requiring at least 4 of the 11 American College of Rheumatology Classification criteria). (E. M. Tan et al., Special article. The 1982 revised criteria for the classification of SLE, Arthritis Rheum. 25:1271–7 [1982]). Siblings of SLE patients who had no positive responses in the Connective Tissue Screening Questionnaire (W. E. Karlson et al., A connective tissue disease screening questionnaire for population studies, Ann. Epidemniol. 5:297–302 [1995]) were classified as unaffected sibs. Multiplex families were recruited by ascertaining nuclear families for two or more SLE patients which were extended to include parents and other siblings.

The subject sample included 78 SLE-affected sibpairs from Caucasian, Asian, and African-American families. All participating members (77 parents, 134 affected and 89 unaffected siblings) were genotyped using 14 microsatellite markers within a 30 cM region (FIG. 1) containing the 15 cM region of human chromosome lq41-q42.

Example 2

Genotyping:

Human genomic DNA was isolated from peripheral blood cells. Microsatellite markers at or near the specific candidate chromosomal region were selected based on the composite map accessible at cedar.genetics.soton.ac.uk/pub/chrom1/gmap. The primers for these marker were purchased from Research Genetics, Inc. (Huntsville, AL). Microsatellite genotyping was determined by scoring the size of PCR products. PCR was performed in a 96-well plate using a thermocycler which was programmed for 950° C. for 1 min, 58° C. for 30 s, and 72° C. for 1 min, with 25 cycles. The labeled PCR products were denatured and separated on a sequencing gel of 5% polyacrylamide and 6 M urea.

To determine genotypes ofPARP, we used the 5' oligonucleotide primer sequence 5'-GAT TCC CCA TCT CTC TTT CTT T-3'(SEQ. ID. NO.:1) tagged with the fluorescent dye 6FAM and the 3' oligonucleotide primer sequence 5'-AAA TTG TGG TAA TGA CTG CA-3' (SEQ. ID. NO.:2). The PCR condition for this polymorphism was 30 cycles of 93° C. for 1 min, 56° C. for 30 s, and 72° C. for 1 min plus a final extension of 72° C. for 5 min. For the intronic dinucleotide repeat of HLX1 the 5' oligonucleotide primer sequence was 5'-TTC ACA CAA GTT CCA GCT TCC CTT-3'(SEQ ID NO:3) tagged with the fluorescent dye TET, and the 3' oligonucleotide primer sequence was 5'-TGC TGT CTC TGT TTC TTT CTG ACC-3'(SEQ ID NO:4). The HLAI PCR condition was 10 cyles of 94° C. for 15 s, 55° C. for 15 s, and 72° C. for 30 s, then followed by 20 cycles of 89° C. for 15s, 55° C. for 15 s and 72° C. for 30 s with a final extension at 72° C. for 10 min. For these two candidate genes, PCR mixture contained 40 ng genomic DNA, 20 mM Tris-HCL pH8.0, 2 mM MgCl$_2$, 10 mM KCl, 6 mM (NH$_4$)$_2$SO$_4$, 0.1% Triton X-100, 10 µg/ml BSA, 0.5 Units of native Pfu DNA polymerase (Stratagene, San Diego, Calif.), 200 µM dNTP, and 0.2 µM primers in 5 µl reaction. Aliquots of fluorescent PCR products were electrophoresed using a 377 Prism ABI sequencer (Applied Biosystems, Foster City, Calif.) and analyzed by GeneScan and Genotyper programs.

Example 3

Data Analysis:

Multipoint linkage analysis of 14 microsatellite markers in the chromosome lq31–42 region and the SLE phenotype (affected or unaffected) was conducted on nuclear families using the MAPMAKERS/SIBS program (L. Kruglyak and E. S. Lander, Complete mullipoint sib-pair analysis of qualitative and quantitative traits, Am. J. Hum. Genet. 57:439–54 [1995]) on a SUN ultra 60 workstation with a UNIX operating system. The program simultaneously uses information at multiple markers in a region to estimate the expected proportions of sib pairs selected for a disorder sharing 0, 1 and 2 alleles identical-by-descent for points along the chromosomal region. A lod score is generated by taking the log of the likelihood of the estimated allele sharing proportion compared to the theoretical likelihood of no linkage to the region. All markers except HLX1 were used in this analysis. The heuristic guideline of one lod below the peak value was used to identify a confidence interval of 5 cM for the location of the SLE susceptibility gene.

The transmission disequilibrium test (TDT; R. S. Spielman et al., Transmission test for linkage disequilibrium of the insulin gene region and insulin-ependent diabetes mellitus [IDDM], Am. J. Hum. Genet. 52:506–16 [1993]) can detect an allelic association with disease in the presence of linkage with the disease. The method involves assessing the transmission of alleles from heterozygous parents to their affected offspring, and testing whether there is evidence that the probability of transmitting the alleles at a marker is different than 0.5 for each allele. The Extended TDT (ETDT; P. C. Sham and D. Curtis, An extended transmission/disequilibrium test [TDT]for multi-allele marker loci, Ann. Hum. Genet. 59:323–336 [1995]), which uses a logistic regression approach to test all alleles at a marker for deviation from a 0.5 transmission probability simultaneously has been used (software provided by the program authors). When a deviation is detected in the overall test it examines each allele separately for a deviation from a 0.5 probability of transmission. The eldest affected individual has been used from each of the nuclear families, as due to linkage with the region, other affected sibs from the same families are not independent of those in this sample.

The relative risk for the 85 bp allele identified by the ETDT at the PARP was assessed using a method described by Weinberg et al. (C. R. Weinberg et al, A log-linear approach to case-parent-triad data: assessing effects of disease genes that act either directly or through maternal effects and that may be subject to parental imprinting, Am. J. Hum. Genet. 62:969–78 [1998]). Poisson regression analysis was applied to data on the numbers of parent-child triads observed among the eldest affected offspring with at least one parent heterozygous for the 85 bp allele. The risk of developing SLE with one or two 85 bp alleles were estimated by using the GENMOD procedure of the statistical Analysis Stems (SAS) package of computer programs.

Example 4

Results

Figure 1:
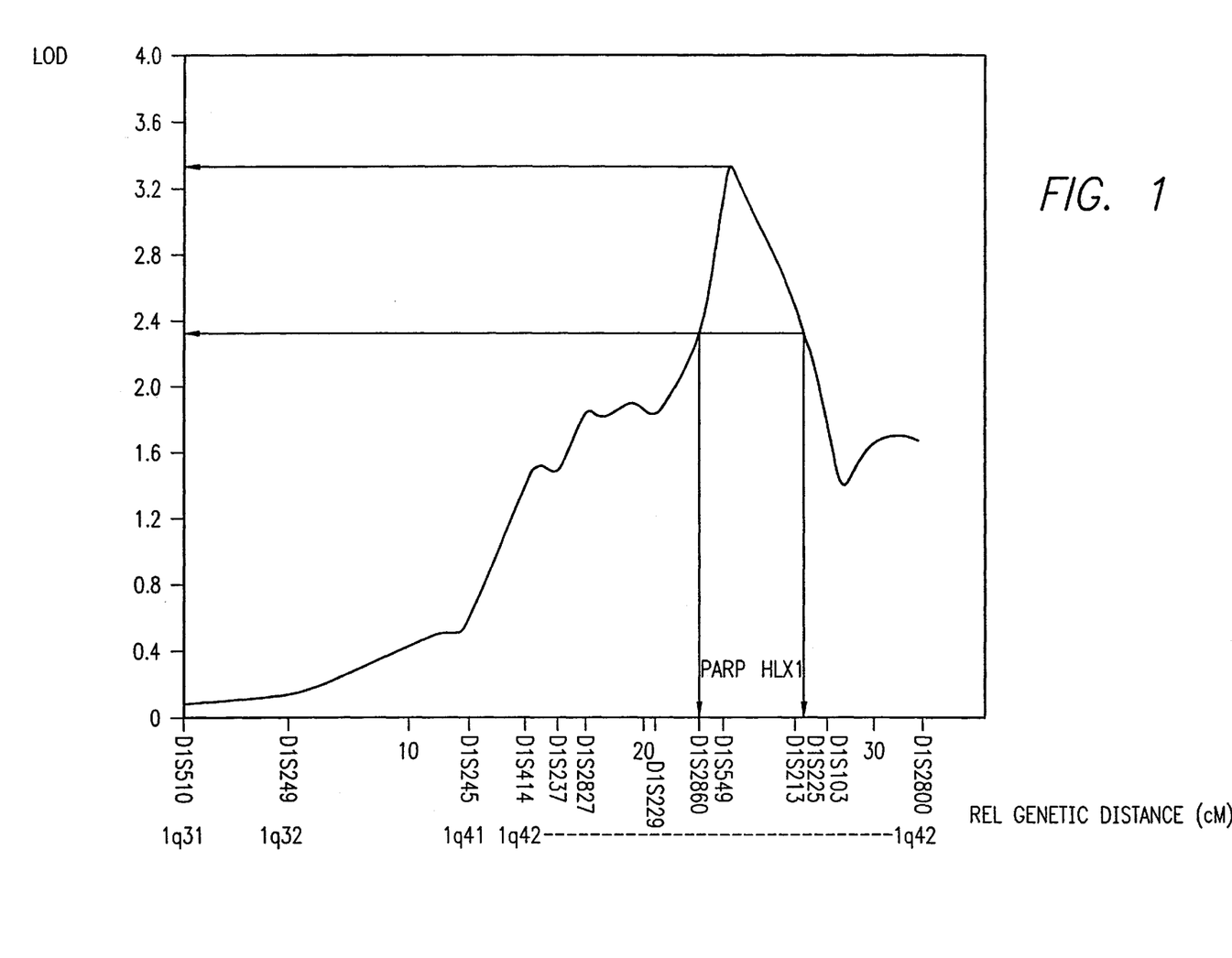
FIG. 1 illustrates the results of multipoint linkage analysis of the chromosome lq31-q42 region using the MAPMAKER/SIBS program. Positions of genetic markers relative to D1S510 are expressed in centiMorgans (cM) as the relative genetic distance shown in the x-axis.

As shown in FIG. 1, multi-point linkage analysis on the current sample using the model-free MAPMAKER/SIBS program identified a peak with a lod score of 3.3 and narrowed the region of interest to approximately 5 cM between microsatellite markers D1S2860 and D1S213.

There were 12 PARP alleles detected in our cohort of 124 multiplex and simplex families. When data from the four most frequent alleles of PARP were analyzed by the multi-allelic TDT, the overall skewing of transmission to affected offspring was evident in the combined sample containing all ethnic groups (p=0.00008) as well as individually in the Caucasian sample (p=0.003) (Table 1). Other ethnic groups were too small in number for valid analysis.

TABLE 1.

Skewed transmission of all analyzed PARP alleles.

| Groups | p-value | |
|---|---|---|
| | affected offspring | unaffected offspring |
| All ethnic groups combined | 0.00008 | 0.02 |
| Caucasians | 0.003 | 0.08 |

Data presented are derived from the four most frequent PARP alleles transmitted and not transmitted from heterozygous parents to offspring in 124 families containing 75 Caucasian, 25 Hispanic, 17 Asian, and 7 African-American. P-value reflects the level of overall departure from the expected random distribution of all ethnic groups combined, or the Caucasian families only, as evaluated by a likelihood ratio test.

Results of a TDT analysis of the four most frequent alleles showed that the 85 bp allele of PARP was preferentially transmitted to affected offspring (transmission: non-transmission=65 :29, p =0.0002) and preferentially not transmitted to unaffected offspring (transmission: non-transmission=25 : 50, p =0.004) (Table 2). The risk of developing SLE with one 85 bp allele compared to having none is 2.3. while it is 4.0 with two 85 bp alleles. The 85 bp allele or polymorphism is a CA repeat located 906 bp upstream of the transcription start site. (See T. Ogura et al. [1990]).

TABLE 2.

Preferential transmission of PARP allele 85 to affected but not to unaffected offspring.

| Alleles | Affected Offspring[a] | | | | Unaffected Offspring[b] | | | |
|---|---|---|---|---|---|---|---|---|
| (bp) | t | nt | % t | p-value | t | nt | % t | p-value |
| 85 | 65 | 29 | 69 | 0.0002 | 25 | 50 | 33 | 0.004 |
| 93 | 23 | 33 | 41 | 0.18 | 21 | 20 | 51 | 0.87 |
| 95 | 12 | 15 | 44 | 0.56 | 16 | 3 | 84 | 0.003 |
| 97 | 17 | 40 | 30 | 0.002 | 30 | 19 | 61 | 0.11 |

[a,b]The oldest affected or unaffected offspring in each family was used for this analysis. Data presented are numbers of times that PARP alleles were transmitted (t) and not transmitted (nt) from heterozygous parents. Data are shown as the percentage transmission of each allele (% t). Each p-value is the level of significance based on a test of the expected random (50%)allele transmission and was evaluated using a chi-squared statistic ($x^2 = [t - nt]^2/(t + nt)$) with 1 degree of freedom).

In contrast, the 97 bp allele of PARP might be protective, as it was preferentially not transmitted to affected offspring (transmission: non-transmission=17: 40, p=0.002)(Table 2).

Similar TDT analyses of HLAI alleles, using an intronic dinucleotide repeat within this gene, yielded no evidence for association with SLE. Transmission data of 7 HLXI alleles to affected offspring from 129 heterozygous Caucasian parents are summarized in Table 3; no significant difference from the expected random distribution was found (the chi-squared for genotype-wise TDT=11.35, p=0.88).

TABLE 3.

HLX1 alleles are not associated with susceptibility to SLE.

| Alleles | Affected Offspring | | |
|---|---|---|---|
| (bp) | t | nt | % t |
| 168 | 9 | 8 | 53% |
| 166 | 10 | 9 | 53% |
| 164 | 8 | 11 | 42% |
| 162 | 17 | 18 | 49% |
| 160 | 30 | 30 | 50% |
| 158 | 39 | 32 | 55% |
| 152 | 16 | 21 | 43% |

The abbreviations (t, nt, % t, and p-value) are the same as those described in Table 2. The analyzed Caucasian families contained 129 heterozygous parents. The overall transmission of 7 tested alleles was not different from the expected random distribution with a p-value of 0.88.

The contrasting TDT results of these two candidate genes, PARP and HLX1 demonstrate that PARP is a susceptibility gene for SLE within the linked lq41-q42 region.

The foregoing examples being illustrative but not an exhaustive description of the embodiments of the present invention, the following claims are presented.

We claim:

1. A method of detecting a genetic predisposition in a human subject to develop systemic lupus erythematosus (SLE), comprising:
   a) collecting a tissue sample from a human subject;
   b) amplifying nucleic acids from said tissue sample using a forward primer having nucleotide sequence GAT TCC CCA TCT CTC TTT CTT T (SEQ. ID. NO. 1) and a reverse primer having nucleotide sequence AAA TTG TGG TAA TGA CTG CA (SEQ ID. NO. 2) to obtain amplification products, said nucleic acids comprising a genomic sequence of human chromosome lq41–q42 between microsatellite markers D1S2860 and D1S213; and
   c) detecting in the amplification products the presence or absence of a fragment of 85-base pair length, the presence of said fragment of 85-base pair length indicating a genetic predisposition in said subject to develop SLE.

2. The method of claim 1, wherein the tissue sample is a blood sample.

3. A method of detecting a genetic predisposition in a human subject to develop systemic lupus erythematosus (SLE), comprising the steps of
   a) collecting a tissue sample from a human subject;
   b) amplifying nucleic acids from said tissue sample using a forward primer having a nucleotide sequence GAT TCC CCA TCT CTC TTT CTT T (SEQ. ID. NO. 1) and a reverse primer having a nucleotide sequence AAA TTG TGG TAA TGA CTG CA (SEQ ID. NO. 2) to obtain amplification products, said nucleic acids comprising a genomic sequence of human chromosome lq41–q42 between microsatellite markers D1S2860 and D1S213; and
   c) detecting in the amplification products the presence or absence of a fragment of 97-base pair length, the absence of said fragment of 97-base pair length indicating a genetic predisposition in said subject to develop SLE.

4. The method of claim 3, wherein the tissue sample is a blood sample.

5. An oligonucleotide primer for detecting in a human subject a genetic susceptibility to SLE, said primer comprising the oligonucleotide sequence GAT TCC CCA TCT CTC TTT CTT T (SEQ. ID. NO. 1).

6. A primer set for detecting in a human subject a genetic susceptibility to SLE, said primer set having a forward primer comprising nucleotide sequence GAT TCC CCA TCT CTC TTT CTT T (SEQ. ID. NO. 1) or a fragment thereof at least 18 nucleotides long, and a reverse primer comprising nucleotide sequence AAA TTO TGG TAA TGA CTG CA (SEQ ID. NO. 2) or a fragment thereof at least 18 nucleotides long.

7. A genetic testing kit for detecting in a human subject a genetic susceptibility to SLE, comprising the primer set of claim 6.

* * * * *

UNITED STATES PATENT AND TRADEMARK OFFICE
CERTIFICATE OF CORRECTION

| | |
|---|---|
| PATENT NO. | : 6,280,941 B1 |
| APPLICATION NO. | : 09/280181 |
| DATED | : August 28, 2001 |
| INVENTOR(S) | : Betty P. Tsao et al. |

It is certified that error appears in the above-identified patent and that said Letters Patent is hereby corrected as shown below:

Beginning at Col 1 lines 2-3, under the title, please insert the following:

--GOVERNMENT LICENSE RIGHTS

The U.S. Government has a paid-up license in this invention and the right in limited circumstances to require the patent owner to license others on reasonable terms as provided for by the terms of Grant No. NIAMS AR 43814 awarded by the National Institutes of Health.--

Signed and Sealed this

Sixth Day of April, 2010

David J. Kappos
*Director of the United States Patent and Trademark Office*

SEQUENCE LISTING

<160> NUMBER OF SEQ ID NOS: 4

<210> SEQ ID NO 1
<211> LENGTH: 22
<212> TYPE: DNA
<213> ORGANISM: Homo sapiens

<400> SEQUENCE: 1
gattccccat ctctctttct tt                                            22

<210> SEQ ID NO 2
<211> LENGTH: 20
<212> TYPE: DNA
<213> ORGANISM: Homo sapiens

<400> SEQUENCE: 2

```
aaattgtggt aatgactgca                                              20

<210> SEQ ID NO 3
<211> LENGTH: 24
<212> TYPE: DNA
<213> ORGANISM: Homo sapiens

<400> SEQUENCE: 3
ttcacacaag ttccagcttc cctt                                         24

<210> SEQ ID NO 4
<211> LENGTH: 24
<212> TYPE: DNA
<213> ORGANISM: Homo sapiens

<400> SEQUENCE: 4
tgctgtctct gtttctttct gacc                                         24
```